US010039820B2

(12) United States Patent
Coller et al.

(10) Patent No.: US 10,039,820 B2
(45) Date of Patent: Aug. 7, 2018

(54) WEST NILE VIRUS VACCINE COMPRISING WN-80E RECOMBINANT SUBUNIT PROTEIN

(71) Applicant: HAWAII BIOTECH, INC., Honolulu, HI (US)

(72) Inventors: Beth-Ann Coller, West Point, PA (US); Vidya Pai, Bethesda, MD (US); Carolyn L. Weeks-Levy, Honolulu, HI (US); Steven A. Ogata, Kailua, HI (US)

(73) Assignee: Hawaii Biotech, Inc., Honolulu, HI (US)

( * ) Notice: Subject to any disclaimer, the term of this patent is extended or adjusted under 35 U.S.C. 154(b) by 0 days.

(21) Appl. No.: 15/331,596

(22) Filed: Oct. 21, 2016

(65) Prior Publication Data
US 2017/0165349 A1 Jun. 15, 2017

Related U.S. Application Data

(63) Continuation of application No. 13/322,784, filed as application No. PCT/US2010/001608 on Jun. 1, 2010, now abandoned.

(60) Provisional application No. 61/182,754, filed on May 31, 2009.

(51) Int. Cl.
*A61K 39/12* (2006.01)
*A61K 39/00* (2006.01)

(52) U.S. Cl.
CPC ........ *A61K 39/12* (2013.01); *A61K 2039/545* (2013.01); *A61K 2039/55505* (2013.01); *C12N 2770/24134* (2013.01)

(58) Field of Classification Search
CPC .............. A61K 39/12; A61K 2039/545; A61K 2039/55505; C12N 2770/24134
See application file for complete search history.

(56) References Cited

U.S. PATENT DOCUMENTS

| | | | | |
|---|---|---|---|---|
| 6,136,561 | A | 10/2000 | Ivy et al. | |
| 6,165,477 | A | 12/2000 | Ivy et al. | |
| 6,432,411 | B1 | 8/2002 | Ivy et al. | |
| 2005/0287170 | A1* | 12/2005 | Lieberman ............ | A61K 39/12 424/204.1 |
| 2006/0073164 | A1 | 4/2006 | Tangy et al. | |

FOREIGN PATENT DOCUMENTS

| | | | |
|---|---|---|---|
| WO | WO 2004/052293 A2 | 6/2004 | |
| WO | WO 2006/0115548 | 11/2006 | |

OTHER PUBLICATIONS

Ledizet, M., et al., 2005, A recombinant envelope protein vaccine against West Nile virus, Vaccine 23:3915-3924.*

Beasley, et al.: *"Protection Against Japanese Encephalitis Virus Strains Representing Four Genotypes by Passive Transfer of Sera Raised Against ChimeriVax-JE Experimental Vaccine";* Vaccine, 2004, pp. 3722-3726, vol. 22.

Ben-Nathan et al.: *"Prophylactic and Therapeutic Efficacy of Human Intravenous Immunoglobulin in Treating West Nile Virus Infection in Mice";* J. Inf. Diseases, pp. 5-12. vol. 188.

Blanchard, 0. L. et al.: *"Translating dosages from animal models to human clinical trials—revisiting body surface area scaling";* FASEB Journal, vol. 29, No. 5, Feb. 5, 2015, pp. 1629-1634.

Bonafe, Nathalie et al.: *"A recombinant West Nile virus envelope protein vaccine candidate produced in Spodoptera frugiperda expresSF± cells";* Vaccine, 2009, vol. 27, pp. 213-222.

Bray et al.: *"Monkeys Immunized With Intertypic Chimeric Dengue Viruses Are Protected Against Wild-Type Virus Challenge, Journal of Virology";* 1996, pp. 4162-4166, vol. 70, No. 6.

Chambers et al., *"Flavivirus Genome Organization, Expression, and Replication";* Annu. Rev. Microbiol., 1990, pp. 649-688, vol. 44.

Diamond et al., *"The Structural Immunology of Antibody Protection Against West Nile Virus";* Immunol. Rev., 2008, pp. 212-225, vol. 225.

European Examination Report dated May 31, 2016, regarding EP Patent Application No. 10 783 708.0.

Huang, O. et al.: *"The application of allometric scaling principles to predict pharmacokinetic parameters across species";* Expert Opinion on Drug Metabolism & Toxicology, vol. 10, Issue 9, Jan. 1, 2014 pp. 1241-1253.

Ings , R.M.J.: *"Interspecies scaling and comparisons in drug development and toxicokinetics";* Xenobiotica, vol. 20, Issue 11, Jan. 1, 1990, pp. 1201-1231.

Kreil et al.: *"Neutralizing Antibodies Protect Against Lethal Flavivirus Challenge But Allow for the Development of Active Humoral Immunity to a Nonstructural Virus Protein";* Journal of Virology, 1998, pp. 3076-3081, vol. 72, No. 4.

Ledizet, M. et al.: *"A recombinant envelope protein vaccine against West Nile virus";* Vaccine. 2005, pp. 233915-233924.

Mahmood et al.: *"Application of allometric principles for the prediction of pharmacokinetics in human and veterinary drug development";* Advanced Drug Delivery Reviews, vol. 59, Sep. 30, 2007, pp. 1177-1192.

Markoff, L.: *"Points to Consider in the Development of a Surrogate for Efficacy of Novel Japanese Encephalitis Virus Vaccines";* Vaccine, 2000, pp. 26-32, vol. 18.

Martin et al.: *"A West Nile Virus DNA Vaccine Induces Neutralizing Antibody in Healthy Adults During a Phase 1 Clinical Trial";* J. Infect. Dis, 2007, pp. 1732-1740, vol. 196.

Mason et al.: *"Molecular Characterization of a Neutralizing Domain of the Japanese Encephalitis Virus Structural Glycoprotein";* J. Gen Virol, 1989, pp. 2037-2049, vol. 70.

(Continued)

*Primary Examiner* — Jeffrey Parkin
(74) *Attorney, Agent, or Firm* — DLA Piper LLP (US)

(57) ABSTRACT

A West Nile virus vaccine for human use is described that preferably contains a recombinantly produced form of truncated West Nile virus envelope glycoprotein and aluminum adjuvant. The vaccine is acceptable for use in the general population, including immunosuppressed, immunocompromised, and immunosenescent individuals. The vaccine is safe and effective for use in all healthy and at-risk populations. A pharmaceutically acceptable vehicle may also be included in the vaccine.

7 Claims, 5 Drawing Sheets

(56) References Cited

OTHER PUBLICATIONS

Monath et al.: *"A Live, Attenuated Recombinant West Nile Virus Vaccine"*; Proc. Natl. Acad. Sci., 2006, pp. 6694-6699, vol. 103, No. 17.

Morrey et al.: *"Humanized Monoclonal Antibody Against West Nile Virus Envelope Protein Administered After Neuronal Infection Protects Against Lethal Encephalitis in Hamsters"*; JID, 2006, pp. 1300-1308, vol. 194.

Putnak et al.: *"DNA Vaccines for Flaviviruses"*; Adv. Virus Res. 2003, pp. 445-468, vol. 61.

Sharma, Vijay et al.: *"To scale or not to scale: the principles of dose extrapolation"'*—British Journal of Pharmacology, Jan. 1, 2009, 157; pp. 907-921.

View of NCT00707642 on Dec. 1, 2008, clinicaltrials.gov Archive, Dec. 1, 2008, URL http://clinicaltrials.gov/archive/NCT00707642/2008_12_01.

Indian Examination Report dated Oct. 25, 2017, regarding IN 9368/DELNP/2011.

\* cited by examiner

Amino Acid Sequence of WN-80E Recombinant Subunit Protein

```
Phe Asn Cys Leu Gly Met Ser Asn Arg Asp Phe Leu Glu Gly Val
1               5                   10                  15

Ser Gly Ala Thr Trp Val Asp Leu Val Leu Glu Gly Asp Ser Cys
                20                  25                  30

Val Thr Ile Met Ser Lys Asp Lys Pro Thr Ile Asp Val Lys Met
                35                  40                  45

Met Asn Met Glu Ala Ala Asn Leu Ala Glu Val Arg Ser Tyr Cys
                50                  50                  60

Tyr Leu Ala Thr Val Ser Asp Leu Ser Thr Lys Ala Ala Cys Pro
                65                  70                  75

Thr Met Gly Glu Ala His Asn Asp Lys Arg Ala Asp Pro Ala Phe
                80                  85                  90

Val Cys Arg Gln Gly Val Val Asp Arg Gly Trp Gly Asn Gly Cys
                95                  100                 105

Gly Leu Phe Gly Lys Gly Ser Ile Asp Thr Cys Ala Lys Phe Ala
                110                 115                 120

Cys Ser Thr Lys Ala Ile Gly Arg Thr Ile Leu Lys Glu Asn Ile
                125                 130                 135

Lys Tyr Glu Val Ala Ile Phe Val His Gly Pro Thr Thr Val Glu
                140                 145                 150
```

FIG. 1A

Ser His Gly Asn Tyr Ser Thr Gln Val Gly Ala Thr Gln Ala Gly
                155                 160                 165

Arg Phe Ser Ile Thr Pro Ala Ala Pro Ser Tyr Thr Leu Lys Leu
                170                 175                 180

Gly Glu Tyr Gly Glu Val Thr Val Asp Cys Glu Pro Arg Ser Gly
                185                 190                 195

Ile Asp Thr Asn Ala Tyr Tyr Val Met Thr Val Gly Thr Lys Thr
                200                 205                 210

Phe Leu Val His Arg Glu Trp Phe Met Asp Leu Asn Leu Pro Trp
                215                 220                 225

Ser Ser Ala Gly Ser Thr Val Trp Arg Asn Arg Glu Thr Leu Met
                230                 235                 240

Glu Phe Glu Glu Pro His Ala Thr Lys Gln Ser Val Ile Ala Leu
                245                 250                 255

Gly Ser Gln Glu Gly Ala Leu His Gln Ala Leu Ala Gly Ala Ile
                260                 265                 270

Pro Val Glu Phe Ser Ser Asn Thr Val Lys Leu Thr Ser Gly His
                275                 280                 285

Leu Lys Cys Arg Val Lys Met Glu Lys Leu Gln Leu Lys Gly Thr
                290                 295                 300

Thr Tyr Gly Val Cys Ser Lys Ala Phe Lys Phe Leu Gly Thr Pro

FIG. 1B

```
                        305                      310                      315
Ala Asp Thr Gly His Gly Thr Val Val Leu Glu Leu Gln Tyr Thr
                320                      325                      330

Gly Thr Asp Gly Pro Cys Lys Val Pro Ile Ser Ser Val Ala Ser
                335                      340                      345

Leu Asn Asp Leu Thr Pro Val Gly Arg Leu Val Thr Val Asn Pro
                350                      355                      360

Phe Val Ser Val Ala Thr Ala Asn Ala Lys Val Leu Ile Glu Leu
                365                      370                      375

Glu Pro Pro Phe Gly Asp Ser Tyr Ile Val Val Gly Arg Gly Glu
                380                      385                      390

Gln Gln Ile Asn His His Trp His Lys Ser Gly
                395                      400
```

FIG. 1C

Coomassie stained SDS-PAGE gel (A) and Western blot (B) of purified West Nile 80E.

FIG. 2

Virus neutralizing antibody responses induced in human volunteers
vaccinated with the West Nile HBV-002 vaccine formulation.

FIG. 3

WEST NILE VIRUS VACCINE COMPRISING WN-80E RECOMBINANT SUBUNIT PROTEIN

RELATED APPLICATIONS

This application is a continuation of U.S. patent application Ser. No. 13/322,784, filed Nov. 28, 2011, which is a 371 National Stage Application of International Patent Application No. PCT/US2010/001608, filed Jun. 1, 2010, which claims the benefit of U.S. Provisional Patent Application No. 61/182,754, filed May 31, 2009, the disclosures and drawings of which prior application are hereby incorporated by reference in their entireties.

STATEMENT REGARDING FEDERALLY SPONSORED RESEARCH

This invention was made with government support under NS052139-04 and W81XWH-06-2-0035 awarded by NIH and the DoD, respectively. The government has certain rights in the invention.

SEQUENCE LISTING

The material in the accompanying Sequence Listing is hereby incorporated by reference into this application.

FIELD OF THE INVENTION

The invention relates generally to the field of vaccines. The present invention relates to a vaccine designed to protect humans from disease caused by the West Nile virus. Specifically, the vaccine comprises a truncated version of the recombinant envelope (E) glycoprotein from West Nile virus produced in an insect cell production system and an aluminum-based adjuvant.

BACKGROUND OF THE INVENTION

The family Flaviviridae includes the prototype yellow fever virus (YFV), the four serotypes of dengue virus (DENY-1, DENV-2, DENV-3, and DENV-4), Japanese encephalitis virus (JEV), tick-borne encephalitis virus (TBEV), West Nile virus (WNV), Saint Louis encephalitis virus (SLEV), and about 70 other disease causing viruses. *Flaviviruses* are small, enveloped viruses containing a single, positive-strand RNA genome. Ten gene products are encoded by a single open reading frame and are translated as a polyprotein organized in the order: capsid (C), "preMembrane" (prM, which is processed to "Membrane" (M) just prior to virion release from the cell), "envelope" (E), followed by non-structural (NS) proteins NS1, NS2a, NS2b, NS3, NS4a, NS4b and NS5 (reviewed in Chambers, T. J. et al., *Annual Rev Microbiol* (1990) 44:649-688; Henchal, E. A. and Putnak, J. R., *Clin Microbiol Rev.* (1990) 3:376-396). Individual flaviviral proteins are then produced through precise processing events mediated by host as well as virally encoded proteases.

The envelope of flaviviruses is derived from the host cell membrane and contains the virally-encoded membrane-anchored membrane (M) and envelope (E) glycoproteins. The E glycoprotein is the largest viral structural protein and contains functional domains responsible for cell surface attachment and intra-endosomal fusion activities. It is also a major target of the host immune system, inducing the production of virus neutralizing antibodies, which are associated with protective immunity.

West Nile virus has become an emerging infectious disease in the United States. The virus infects birds, which serve as the natural reservoir for the virus, in addition to humans and horses, which are incidental hosts. It is an arthropod-borne virus transmitted by over 42 species of mosquitoes from various genera including the genus Culex. The first documented case of WNV was found in the West Nile region of Uganda in 1937 (Smithburn et al., *Am J Trop Med Hyg* (1940) 20:471-492). It has since spread through the Middle East, Oceania, parts of Europe and Asia, and has recently emerged in the Americas. Since the first case of human infection in the U.S. was documented in New York City in 1999, the virus rapidly spread throughout the East coast of the U.S. and has spread west across the continent. It has now been found in bird populations in all 48 continental states. Human cases of WN disease have been documented in 47 of the 50 states, with only Alaska, Hawaii and Maine having no reported human cases (*MMWR*, 2008, 57(26):720-23).

The majority of individuals infected with WNV experience flu-like symptoms. However, a number of infected individuals will develop severe disease which carries a case-fatality rate of 3-15% and is highest among the elderly. In addition, in a high percentage of the non-fatal cases, permanent neurological disabilities result. In 2003, of 9,862 symptomatic infected individuals, 2,866 (29%) had neuroinvasive disease (defined as West Nile meningitis, encephalitis and myelitis) and 264 died from the disease. Neuroinvasive complications rose to 36% in 2004 (*MMWR*, vol. 53 Nov. 19, 2004). Recent studies have shown that recovery from viral infection requires significantly more time than originally thought. One study has concluded that the median recovery time was 60 days (Comment, *Ann Inter. Med.* (2004), 141:153) while another documented that only 37% of patients recovered completely after one year (Klee et al., *Emerg. Inf. Dis.* (2004) 10:1405-1411). The neurological damage done by the virus is slow to heal and, in some cases, is permanent. In recent years, some individuals have suffered from polio-like symptoms of acute flaccid paralysis. The clinical findings are significantly worse in elderly patients. In a study of a recent outbreak of WNV infections in Israel, within the study group of 233 hospitalized patients, there was an overall case fatality rate of 14%. However, among patients aged 70 or older, the case fatality rate was 29% (Chowers et al., *Emerg. Inf Dis.* (2001) 7:675-78). Similar findings were also reported from recent epidemics in Romania (Tsai et al., *Lancet* (1998) 352:767-771) and Russia (Platonov et al., *Emerg. Inf. Dis.* (2001) 7:128-32). Thus, there is significant morbidity and mortality associated with WN disease, especially among the elderly/immunosenescent, immunocompromised, and immunosuppressed populations.

The WNV envelope protein shares significant homology with the envelope proteins of other flaviviruses, particularly those in the Japanese encephalitis (JE) serocomplex: JEV, St. Louis encephalitis (SLEV), and Murray Valley encephalitis (MVEV) viruses. Antibodies directed against particular epitopes contained within the envelope protein are capable of viral neutralization, i.e., the inhibition of virus infection of susceptible cells in vitro. Neutralizing antibody epitopes have been mapped to all three domains of the E glycoprotein of flaviviruses, including WNV (Diamond et al., *Immunol. Rev.* (2008) 225:212-25). A high titer of viral neutralizing antibodies is generally accepted as the best in vitro correlate of in vivo protection against flavivirus infection and the resultant disease (Markoff *Vaccine* (2000) 18:26-32; Ben-Nathan et al., *J Inf. Diseases* (2003) 188:5-12; Kreil et al., *J. Virol.* (1998) 72:3076-3081; Beasley et al., *Vaccine* (2004) 22:3722-26). Therefore, a vaccine that induces high titer WNV neutralizing antibody responses will likely protect vaccines against disease induced by WNV.

To date the development of flavivirus vaccines has met with mixed success. There are four basic approaches that have been implemented in an effort to produce vaccine candidates to protect against disease causes by flaviviruses. The four methods are live-attenuated virus, inactivated whole virus, recombinant subunit protein, and DNA. The live-attenuated virus vaccine developed for YFV has been available for many decades and demonstrates the utility of this approach. The use of inactivated whole virus vaccines has been demonstrated for TBEV and JEV with registered products available for both of these disease targets based on this approach.

As described above, there has been success in developing vaccines for YFV, JEV, and TBEV. However, the use of live-attenuated virus and inactivated virus methods to develop vaccines for other flaviviruses has met significant challenges. For example, a significant amount of effort has been invested in developing candidate live-attenuated dengue vaccine strains; however, many of the strains tested have proven unsatisfactory (see, e.g., Eckels, K. H. et al., *Am. J Trop. Med. Hyg.* (1984) 33:684-689; Bancroft, W. H. et al., *Vaccine* (1984) 149:1005-1010; McKee, K. T., et al., *Am. J Trop. Med. Hyg.* (1987) 36:435-442). Despite these initial unsatisfactory results, efforts to develop and test dengue live-attenuated candidate vaccine strains continue (Reviewed in *Am. J. Trop. Med. Hyg.* (2003) 69:1-60). No significant efforts to develop a WNV vaccine utilizing traditional live-attenuated methods have been made.

As an alternative to traditional live-attenuated methods to develop flavivirus vaccines, recombinant chimeric methods have been utilized. This method utilizes a known live-attenuated flavivirus strain as a base and the appropriate genes (prM and E for flaviviruses) from a related virus of interest are substituted for the equivalent genes of the base virus. One approach that has been used for WNV and DENY vaccine development is use of an intertypic chimeric based on an attenuated DENV-4 strain (Bray, M: et al., *J. Virol.* (1996) 70:4162-4166; Chen, W., et at, *J. Virol.* (1995) 69:5186-5190; Bray, M. and Lai, C.-J., *Proc. Natl. Acad. Sci. USA* (1991) 88:10342-10346; Lai, C. J. et at, *Clin. Diagn. Virol.* (1998) 10:173-179). Another approach has been the use of the YFV 17D attenuated strain as a base to develop recombinant chimeric vaccines for JEV, DENY, and WNV (Lai, C. J. and Monath T. P. *Adv Virus Res* (2003) 61:469-509; Monath et al. *Proc. Natl. Acad. Sci. USA* (2006) 103:6694). While the use of live-attenuated chimeric methods has advantages over traditional live-attenuated methods, the chimeric methods are still plagued by difficulties faced in developing properly attenuated strains and in the case of a DENY vaccine achieving balanced, tetravalent responses against the four dengue viruses. Furthermore, live-attenuated approaches may not be appropriate for vaccines targeting encephalitic diseases due to an elevated risk factor or for target populations with compromised immune systems. Both of these factors are applicable to WNV vaccine development.

Currently there are commercially available vaccines produced for JE and TBE utilizing the whole inactivated virus methods. As with live-attenuated virus methods, the use of inactivated virus methods for certain flaviviruses has not guaranteed success with other flaviviruses. For example, efforts to develop inactivated DENV or WNV vaccines have met with limited success. This method is limited by the ability to obtain adequate viral yields from cell culture systems. Virus yields from insect cells such as C6/36 cells are generally in the range of $10^4$ to $10^5$ pfu/ml, well below the levels necessary to generate a cost-effective inactivated virus vaccine. Yields from mammalian cells including LLC-MK2 and Vero cells are higher, but the peak yields, approximately $10^6$ pfu/ml from a unique Vero cell line, are still lower than necessary to achieve a cost-effective vaccine product.

The use of naked DNA methods has also been evaluated in an effort to develop non-replicating flavivirus vaccines for DENV, JEV, TBEV and WNV (Reviewed in Putnak, R. et al. (2003) *Adv. Virus Res.* 61:445-68). The DNA method offers advantages in ease of production, use of defined sequences, potential to elicit both humoral and cellular immunity due to the expression of virus antigens in vivo. Despite these advantages, the ability to induce consistent and robust immune responses in humans, particularly antibody responses, continues to be a major hurdle to this approach. Additionally, DNA vaccines face additional regulatory scrutiny due to concerns about integration of plasmid sequences in the host genome and the potential of generating auto-antibodies to double stranded DNA. To date no DNA vaccine has been approved for human use and it is not clear that this approach will ever be deemed appropriate for a prophylactic human vaccine.

The use of recombinant subunit proteins for flavivirus vaccine development is another example of a non-replicating virus approach. This approach offers advantages in production of well defined products and the potential to elicit specific immune responses. While the potential to generate relevant and robust immune responses exist, there are challenges associated with use of recombinant subunit protein vaccines. This is due to both the quality of the proteins (native-like structure) and the need for adjuvants in eliciting the desired immune responses. Recombinant subunit protein vaccines have a long history of safety and protective efficacy, illustrated most effectively by the recombinant subunit Hepatitis B vaccines (e.g. Engerix B® and Recombivax HB®), and more recently by the human papilloma virus vaccines (e.g. Gardasil® and Cervarix®). The fact that there is no replicating virus present at any time during production, helps assure that there is very limited risk associated with the administration of the subunit vaccine to healthy or immunocompromised individuals in a prophylactic setting. Moreover, the Hepatitis B and human papillomavirus vaccines have been shown to be highly immunogenic and efficacious.

The expression of recombinant flavivirus proteins has focused on the structural proteins C, prM and E and the non-structural protein NS1. The E protein has been the subject of most efforts as this protein is exposed on the surface of the virus, is involved in important biological aspects of the virus life cycle (e.g. binding to receptors and mediating fusion), and is the target of neutralizing antibodies in infected hosts (Chambers, supra; Mason, P. W., *J. Gen Virol* (1989) 70:2037-2048). Furthermore, monoclonal antibodies directed against purified flavivirus E proteins are neutralizing in vitro and some have been shown to confer passive protection in vivo (Henchal, E. A. et al., *Am. J. Trop. Med. Hyg.* (1985) 34:162-169; Heinz, F. X. et al., *Virology* (1983) 130:485-501; Kimura-Kiroda, J. and Yasui, K., *J Immunol.* (1988) 141:3606-3610; Trirawatanapong, T. et al., *Gene* (1992) 116:139-150; Money, J. D. et al., *J. Inf. Dis* (2006) 194:1300-8).

A variety of expression systems such as *E. coli*, yeast, and baculovirus have been utilized for the production of recombinant flavivirus proteins for use in vaccines. These attempts have been plagued by low yields, improper processing of the flavivirus proteins, and moderate to poor immunogenicity (Eckels, K H and Putnak, R, *Adv. Virus Res.* (2003) 61:395-418). Work at Hawaii Biotech, Inc. (HBI) on expression of recombinant E subunit proteins has established the need to maintain the native-like structure of the E protein in order for the recombinant proteins to serve as potent immunogens. The ability to produce recombinant E proteins with native-like structure is highly dependent on the expression system utilized. U.S. Pat. No. 6,165,477 discloses the process for expression of DENV E protein subunits in yeast cells. The E subunits expressed in yeast cells demonstrated improved structure over bacterial systems, but still faced problems with hyper-glycosylation, yields, and product uniformity.

In more recent studies, it has been established that the use of stably transformed insect cells to express truncated forms of the E protein results in uniform products that maintain native-like structure as determined by X-ray crystallography (Modis, Y. et al, *Proc. Natl. Acad. Sci. USA* (2003) 100: 6986-91; Modis, Y. et al, *Nature* (2004) 427:313-19; and Zhang, Y. et al, *Structure* (2004) 12:1607-18). The use of the stably transformed insect cell system has resulted in successful expression of truncated recombinant E subunit proteins from DENV-1, -2, -3, -4, JEV, TBEV and WNV. U.S. Pat. No. 6,136,561 discloses the process for expression of DENV, JEV, TBEV and YFV recombinant E subunit proteins in stably transformed insect cells. U.S. Pat. No. 6,432,411 discloses the utility of flavivirus E recombinant subunit proteins expressed in stably transformed insect cells as candidate vaccines when combined with saponin containing ISCOM-like structures. Preclinical evaluation of the truncated recombinant WNV envelope subunit protein (WN-80E) and non-structural 1 protein (WN-NS1) produced by stably transformed insect cell lines has been recently reported (Lieberman et al, *Vaccine* (2008) 25:414-423; Watts et al, *Vaccine* (2007) 25:2913-2918; Siirin et al., *Am. J Trop. Med. Hyg*. (2008) 79:955-962). In these reports combinations of E and NS1 formulated with saponin containing adjuvants are evaluated in mice and hamster models to evaluate protective efficacy. These patents and publications demonstrate the utility of the flavivirus recombinant subunit proteins expressed from stably transformed insect cells when combined with saponin containing adjuvants to generate appropriate antibody responses in animal models. U.S. Pat. No. 6,432,411 along with Lieberman et al. 2007 (supra) and Watts et al. 2007 (supra) also demonstrate the benefit of including recombinant NS1 in the vaccine formulation in animal models. However, these patents and publications do not address or predict a vaccine formulation based solely on E that has demonstrated applicability for human use.

In general the use of non-replicating virus vaccine approaches such as inactivated virus, recombinant subunit protein, and DNA have several advantages over the live-attenuated virus vaccine approaches. Primarily these advantages are related to safety, as no live virus is delivered to subjects, and to the ability to modulate and balance immune responses by adjusting dosage.

In the development of flavivirus vaccines for humans it has been difficult to predict safety and immunogenicity of candidate vaccines in human subjects based on preclinical data in animal models. This has proved challenging for many of the live-attenuated virus vaccine candidates that have advanced to human clinical trials. The most glaring example of a complete failure was the safety profile exhibited by a cloned dengue virus type 3 isolate which displayed a very attractive safety profile in non-human primates, but which induced dengue fever in vaccine recipients in Hong Kong (Sanchez et al., *FEMS Immunol. Med. Microbiol.* (2006) 24:4914-26). This challenge may be decreased by use of non-replicating virus vaccines which do not require the same level of virus/host interactions in order to achieve vaccine efficacy as replicating virus vaccines. However, there are numerous examples of non-replicating virus vaccine candidates which have shown good safety and protective efficacy in preclinical models, which failed to function as safe and effective vaccines in humans (e.g. inactivated RSV vaccine; Murphy et al., *J. Clin. Microbiol.* (1986) 24:197-202). Thus, there can be multiple challenges associated to developing safe and effective vaccines for flaviviruses and development often requires years of trial and error. Furthermore, preclinical studies based on animal models may not be predictive of vaccine performance in human subjects; and therefore, human data is critical in demonstrating the utility of a candidate vaccine.

While there are several investigational WNV vaccines in various stages of preclinical research and development, there are only three vaccine candidates that have previously been reported to have advanced to human clinical trials. The three vaccines that have been tested in clinical studies are: (1) a live, attenuated dengue serotype 4-West Nile chimera (Pletnev et al, *Proc. Natl. Acad. Sci. USA* (2002) 99:3036-41); (2) a live, attenuated Yellow Fever-West Nile chimera (Chimerivax; Monath et al., *Proc. Natl. Acad. Sci. USA* (2006) 103:6694); and (3) a "naked" DNA vaccine encoding the prM and E genes (Martin et al., *J. Infect. Dis*. (2007) 196:1732-40). There are intrinsic difficulties and potential shortcomings associated with each of the three candidate vaccines.

The first two vaccines being tested clinically are both live-attenuated vaccines. Safety concerns are paramount with all live viral vaccines given to healthy subjects. Under-attenuation of the virus may result in virus-related adverse events, whereas over-attenuation may abrogate vaccine efficacy. Also, reversion to wild type or mutation to increased virulence (or decreased efficacy) may occur. Moreover, even if properly attenuated, live viral vaccines are contraindicated for specific patient populations, such as immune deficient or immune suppressed patients, as well as particular segments of the normal population, such as pregnant women or elderly individuals. Particularly worrisome with the Chimerivax technology is the safety profile of the YF 17D vaccine (which serves as the backbone for the chimera) in the elderly and immunocompromised. Since the late 1990s a number of cases of fatal, disseminated, viscerotropic and neurotropic vaccine virus infections have been documented, particularly among the elderly and immunocompromised. This has led to recommendations against use of the YF 17D vaccine in these populations unless the risk of YF virus infection is very high (Barrett, ADT and Teuwen, DE (2009) *Curr. Opin. Immunol.* 21:308-13). In light of the key association between morbidity and mortality of WNV infection in elderly subjects, the application of a live attenuated vaccine approach to this disease target is highly questionable from a safety perspective and thus the first two vaccine candidates do not offer a safe solution to the need for a West Nile vaccine.

The third West Nile vaccine that has been tested in clinical trials is a DNA vaccine. Naked DNA vaccines are unproven for any infectious disease at this time, and the issue of potential immunopathology due to the induction of an autoimmune reaction to the DNA over the long term is unresolved. The results of the WNV DNA vaccine clinical trial were recently reported (Martin et al, *J Infect Dis* (2007) 196:1732). Low levels of neutralizing antibodies were elicited; however, clinical development of this DNA vaccine has apparently been abandoned, likely linked to safety challenges. Thus, DNA vaccines do not offer a safe and effective solution for development of a WNV vaccine for human use.

As described above, efforts have been made to produce a vaccine that protects humans against disease caused by WNV infection that is both safe and sufficiently immunogenic. Despite these efforts, a WNV vaccine for human use that fully meets these conditions has yet to be established. Therefore, the technical problem to be solved by the invention is the discovery of a WNV vaccine that satisfies two major conditions; the ability to (1) induce relevant protective immune responses in vaccinated individuals (human subjects), and (2) maintain an exceptional safety profile in human subjects in light of the key at-risk population which includes elderly and immunocompromised. This represents a significant challenge in WNV vaccine development, and to date no vaccine approach has been shown to adequately address all aspects of this technical problem. There is an unmet and growing demand, for a solution as the prevalence of West Nile viral infection spreads.

SUMMARY OF THE INVENTION

The present invention provides a unique human vaccine to protect against disease associated with WNV infection. The vaccine is formed by the combination of a recombinant subunit protein derived from WNV envelope protein and aluminum hydroxide adjuvant. The vaccine is capable of inducing a relevant protective immune response and has demonstrated an acceptable safety profile in vaccinated human volunteers. This unique vaccine formulation depends upon a novel, properly folded recombinant envelope subunit protein ("West Nile 80E" or "WN-80E") combined with an aluminum-based adjuvant to produce the vaccine formulation HBV-002. This vaccine (1) induces relevant, protective immune responses, such as virus neutralizing antibody in healthy human volunteers and (2) maintains an acceptable safety profile for administration to healthy and immunocompromised individuals.

Other aspects of this invention include use of a therapeutically effective amount of the vaccine in an acceptable carrier for use as an immunoprophylactic against disease caused by WNV infection and a therapeutically effective amount of the vaccine in an acceptable carrier as a pharmaceutical composition.

BRIEF DESCRIPTION OF THE DRAWINGS

FIG. 1. Amino Acid Sequence of WN-80E Recombinant Subunit Protein (SEQ ID NO: 1). Amino acid numbers are indicated starting at the amino terminus of the protein.

FIG. 2. Coomassie stained SDS-PAGE gel (A) and Western blot (B) of purified West Nile 80E. All samples were run under non-reducing conditions on 10% gels. The Western blot was developed using a rabbit polyclonal antisera developed against West Nile virus. The sizes of the molecular weight markers (in kD) are indicated to the left of the gel and blot. The sample loadings (in μg) are indicated at the top of each lane.

FIG. 3. Virus neutralizing antibody responses induced in human volunteers vaccinated with the West Nile HBV-002 vaccine formulation.

DETAILED DESCRIPTION OF THE INVENTION

The invention described herein provides a vaccine for humans that protects against disease that results from infection with the West Nile virus. The vaccine comprises a WNV recombinant subunit envelope glycoprotein (WN-80E) and aluminum adjuvant. The described vaccine formulation for human use is referred to as HBV-002. HBV-002 is effective in inducing a strong virus neutralizing antibody response in human volunteers. Furthermore, HBV-002 has an acceptable safety profile for healthy and at-risk human subjects.

West Nile Virus Envelope Protein Subunit (WN-80E)

The WNV vaccine of the present invention utilizes the WN-80E recombinant subunit protein that is produced by means of a cell culture expression system that is based on *Drosophila* Schneider 2 (S2) cells. The use of this system results in recombinant envelope subunit proteins that maintain native-like structure. The WNV recombinant envelope protein is truncated at the C-terminus, leaving 80% of the native envelope protein ("80E"). Thus WN-80E is defined as approximately the first 80% of consecutive amino acids of E starting at the first N-terminal amino acid. The C-terminal truncation is designed to delete the membrane anchor portion of the WN E protein (approximately 50 amino acids or 10% from the carboxy terminal end of the full length E protein), in other words, up to the first 90% of consecutive amino acids of WN E protein starting at amino acid 1 of its N-terminus, thus allowing it to be secreted into the extracellular medium and facilitating recovery. More than 90%, but less than 100%, of the E protein can be cloned and secreted, i.e., the protein can be 90%+ in length, carboxy truncated, and can include a portion of the membrane spanning domain so long as the truncated E protein is secretable. "Secretable" means the ability to be secreted; and typically secreted, from the transformed cells of the expression system. The 80E truncation further deletes the "stem" portion of the WN E protein that links the ectodomain of E with the membrane anchor portion. The stem portion does not contain notable antigenic epitopes and therefore is not included.

The preferred antigen for inclusion in the WNV vaccine is WN-80E. The WN-80E recombinant subunit protein expressed in the *Drosophila* S2 expression system is secreted into the culture medium, is properly glycosylated, and maintains native-like conformation as determined by reactivity with the conformationally sensitive monoclonal antibody 4G2. As demonstrated in the present invention, the proper formulation of the recombinant WN-80E subunit protein for human use results in the ability to induce potent virus neutralizing antibodies in human subjects. Thus the WNV vaccine formulation of the invention provides a novel solution to a key technical problem: the production of a West Nile vaccine which demonstrates both a high level of safety and immunogenicity in human subjects.

The preferred vaccine formulation of the present invention includes an adjuvant that is suitable for human use. A preferred adjuvant is an aluminum-based adjuvant (e.g., Alhydrogel™). Formulation with aluminum comprises an admixture whereby the WN-80E antigen is allowed to bind to the Alhydrogel such that ≥75% of the antigen is bound to the aluminum hydroxide.

In a preferred embodiment the WN-80E protein comprises amino acids 1-401 of WNV, strain NY99. The WN-80E amino acid sequence is provided as FIG. 1. The WN-80E protein is preferably produced from vectors containing an appropriate DNA fragment that encodes the WNV prM protein together with the 80E protein. The encoded prM segment is processed by cellular enzymes in the host cells to release the mature WN-80E protein (FIG. 1) in a manner that is similar to that which occurs during maturation of the native WNV. The purified WN-80E product expressed from S2 cells is shown in FIG. 2.

In a further embodiment of the invention, WN-80E is defined more broadly as a West Nile virus envelope protein subunit that comprises six disulfide bridges at Cys1-Cys2, Cys3-Cys8, Cys4-Cys6, Cys5-Cys7, Cys9-Cys10 and Cys11-Cys12; wherein the polypeptide has been secreted as a recombinant protein from *Drosophila* cells; and wherein the polypeptide generates neutralizing antibody responses to West Nile virus when administered to human subjects.

In a more preferred embodiment, the recombinant WNV envelope protein subunit further comprises the disulfide pattern described and a hydrophilicity profile characteristic of a homologous 80% portion of an envelope protein (80E) starting from the first amino acid at the N-terminus of the native WNV envelope protein. In other words, amino acids can be substituted in the sequence comprising WN-80E so long as the disulfide and hydrophilicity profile is maintained to ensure that the recombinant subunit protein retains a native-like structure and appropriate immunogenicity (ability to elicit virus neutralizing antibodies).

Preferably, the WN-80E recombinant subunit protein is expressed using a Master Cell Bank in serum free media and purified by immunoaffinity chromatography (IAC) using a monoclonal antibody (e.g. 4G2) as previously described (Ivy et al., U.S. Pat. No. 6,432,411). This results in a WN-80E product that can be used in vaccine formulation that is suitable for use in humans.

Surprisingly, and in contrast to the added benefit described for inclusion of non-structural proteins such as non-structural protein 1 (NS1) in other flavivirus formulations (McDonell et al., U.S. Pat. No. 6,416,763), the vaccine formulation of the invention which only contains the WN-80E protein serves as a potent, immunogenic vaccine in non-human primates (Lieberman et al., *Clin. Vaccine Immunol.* (2009) 16:1332-37) and human subjects even without inclusion of NS1. The virus neutralizing antibody responses induced in human volunteers vaccinated with the HBV-002 vaccine formulation that contains the WN-80E protein together with an alum-based adjuvant is shown in FIG. 3.

Alum

In a preferred embodiment, the WNV vaccine of the invention comprises WN-80E recombinant subunit protein formulated with aluminum-based adjuvants (collectively, "alum" or "alum-based adjuvants") such as aluminum hydroxide, aluminum phosphate, or a mixture thereof. Aluminum hydroxide (commercially available as "Alhydrogel™") was used for preparation of clinical material and therefore is a preferred form of alum. Aluminum-based adjuvants were the first adjuvants registered for human use in the United States and around the world and their effectiveness is widely recognized. Aluminum-based adjuvants are believed to function at least partially via a depot mechanism and the combination of the recombinant WN-80E antigen with native-like structure and the adjuvant effect of the alum is sufficient to induce a potent immune response in vaccinated individuals, including members of the immunodeficient population. Formulation with alum comprises an admixture whereby the WN-80E antigen is allowed to bind to the Alhydrogel™ such that ≥75% of the antigen is bound to the aluminum hydroxide.

Preferably, the WNV vaccine formulation of WN-80E+ Alhydrogel and filling of vials with the preferred formulation of the vaccine (HBV-002) is conducted under cGMP. This results in a WNV vaccine formulation comprising WN-80E and alum that is suitable for use in humans.

Administration and Use

The present invention provides a means for preventing or attenuating disease that result from infection by WNV. As used herein, a vaccine is said to prevent or attenuate a disease if administration of the vaccine to an individual results either in the total or partial immunity of the individual to the disease, or in the total or partial attenuation (i.e., suppression) of symptoms or conditions associated with the disease.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient. In the present invention the detectable change in the recipient patient is the induction of a neutralizing antibody against WNV.

The active vaccine of the invention can be used alone or in combination with other active vaccines such as those containing other active subunits to the extent that they become available. Corresponding or different subunits from one or several viruses or serotypes may be included in a particular formulation. The active vaccine of the invention may further comprise a pharmaceutically acceptable excipient.

The therapeutic compositions of the described invention can be administered parenterally by subcutaneous, intramuscular, or intradermal injection; however, other systemic modes of administration may also be employed. The preferred method of administration for the present invention is the intramuscular route.

Many different techniques exist for the timing of the immunizations when a multiple administration regimen is utilized. It is preferable to use the compositions of the invention more than once to increase the levels and diversities of expression of the immunoglobulin repertoire expressed by the immunized subject. Typically, if multiple immunizations are given, they will be given one to two months apart. The preferred immunization schedule of the invention is to immunize the subjects a 0, 1, and 2 months. Other immunizations schedules can also be utilized. For example, alternative immunization schedules such as 0, 1 and 3 months, or 0, 1 and 6 months, or 0, 1, 12 months could be used. Additional booster vaccinations may be administered at prescribed intervals such as every 5 to 10 years.

To immunize subjects against WNV-induced disease for example, the vaccine formulation containing the recombinant subunit protein and adjuvant are administered to the subject in conventional immunization protocols involving, usually, multiple administrations of the vaccine. Administration is typically by injection, typically intramuscular or subcutaneous injection; however, other systemic modes of administration may also be employed.

According to the described invention, an "effective amount" of a therapeutic composition is one which is sufficient to achieve a desired biological effect. Generally, the dosage needed to provide an effective amount of the composition will vary depending upon such factors as the subject's age, condition, sex, and extent of disease, if any, and other variables which can be adjusted by one of ordinary skill in the art. The antigenic preparations of the invention can be administered by either single or multiple dosages of an effective amount. Effective amounts of the compositions of the invention can vary from 0.01-100 µg per dose, more preferably from 5-50 µg per dose, and most preferably 15-50 µg per dose. The compositions of the invention may further comprise a pharmaceutically acceptable excipient.

EXAMPLES

The Examples given below provide the basis of the present invention. The examples demonstrate the ability to manufacture the recombinant WN-80E protein and HBV-002 vaccine formulation at large scale and under cGMP to support administration to human subjects (Examples 1-3). The examples further demonstrate the safety and immunogenicity (efficacy) of the vaccine in healthy adult volunteers (Example 4). The safety and efficacy of the HBI WNV vaccine depends on the novel combination of two different aspects. In one aspect, the inherent safety of recombinant subunit proteins combined with aluminum-based adjuvants provide the optimal approach for prevention of a disease which targets elderly and immunocompromised—the particularly frail at-risk population—for the most severe disease. In a second aspect, the production of conformationally relevant (native-like structure) recombinant WN-80E antigen under cGMP, in quantities sufficient to be of practical use, results in a vaccine which induces virus neutralizing antibodies in human subjects, providing a mechanism for protection against disease. The unique combination of these aspects results in the novel invention of a WNV vaccine which is safe and effective in human subjects. These vaccine formulations are further characterized by the unexpected finding that inclusion of the non-structural protein NS1 is not required for effective immunogenicity and protection. Moreover the disclosed West Nile vaccine is uniquely situated to address the technical problem of inducing relevant protective immune responses in vaccinated individuals while maintaining an acceptable safety profile, in particular for those subjects at highest risk of severe disease, the elderly and immunocompromised.

The following examples are intended to illustrate but not to limit the invention.

Example 1

Expression and Purification of West Nile 80E Protein in the *Drosophila* S2 System The expression plasmid pMttbns (derived from pMttPA) contains the following elements: *Drosophila melanogaster* metallothionein promoter, the human tissue plasminogen activator secretion leader (tPAL) and the SV40 early polyadenylation signal. At Hawaii Biotech, a 14 base pair BamHI fragment was excised from the pMttbns vector to yield pMttΔXho that contains a unique XhoI site in addition to an existing unique BglII site. This expression vector promotes the secretion of expressed proteins into the culture medium. West Nile sequences were introduced into the pMttΔXho vector using these unique BglII and XhoI sites. For the expression of a carboxy-truncated West Nile envelope protein, a synthetic gene encoding the entire prM protein and amino acids 1-401 of the E protein from West Nile virus was synthesized (Midland Certified Reagent Co., Midland, Tex.). The nucleotide sequence of the synthetic gene follows the published sequences of West Nile virus isolated in 1999 in New York City. The C-terminal truncation of the E protein at amino acid 401 of the E protein eliminates the transmembrane domain, and therefore can be secreted into the medium. The final prM80E plasmid construct was designated pMttWNprM80E. Upon expression in the S2 cells the prM sequence is cleaved from the 80E sequence by host cell proteases. The 401 amino acid WN-80E recombinant subunit protein is secreted into the culture medium. The amino acid sequence of the WN-80E protein is provided in FIG. 1.

S2 cells were co-transformed with both the pMttWNprM80E expression plasmid and the pCoHygro selection plasmid that encodes hygromycin resistance utilizing the (i) calcium phosphate co-precipitation method or (ii) Cellfectin (Invitrogen Kits, Carlsbad, Calif.) according to the manufacturer's recommendations. Cells were co-transformed with 20 µg total DNA with a 20:1 ratio of expression plasmid to selection plasmid. Transformants were selected with hygromycin B (Roche Molecular Biochemicals, Indianapolis, Ind.) at 300 µg/ml. Following selection, cells were adapted to growth in the serum free medium, Excel 420 (JRH, Lenexa, Kans.). For expression studies, cells were grown in Excel 420, 300 µg/ml hygromycin, and induced with 200 µM CuSO4. Cells were seeded at a density of $2\times10^6$ cells/ml and allowed to grow for 6-7 days. Under optimal conditions, cell densities of greater than $2\times10^7$ cells/ml were achieved after 6-7 days of growth. The culture supernatant was examined for expressed protein by SDS-PAGE and Western blot.

For the detection of WN-80E on Western blots a rabbit polyclonal anti-West Nile virus antibody (BioReliance Corp., Rockville, Md.) or a rabbit polyclonal anti-DEN purified inactivated virus which cross-reacts with West Nile virus E protein was used, followed by an anti-rabbit IgG-alkaline phosphatase conjugated secondary antibody. The blots were developed with NBT/BCIP (Sigma Chem. Co.) solid phase alkaline phosphatase substrate.

Purification of the WN-80E protein was accomplished by immunoaffinity chromatography (IAC) using the monoclonal antibody (MAb) 4G2. Briefly, the procedure involves the clarification of the post-expression medium. The crude material is then loaded onto the IAC column, which contains immobilized MAb that is covalently coupled via N-hydroxy-succinimide chemistry. After the sample is loaded, the matrix is washed with 10 mM phosphate buffered saline (PBS), pH 7.2, containing 0.05% (v/v) tween-20 (PBST, 140 mM NaCl). Bound protein is eluted from the IAC column with 20 mM glycine buffer, pH 2.5. The eluate is neutralized then buffer exchanged against PBS. The purification products are routinely analyzed by sodium dodecyl sulfate polyacrylamide gel electrophoresis (SDS-PAGE) with Coomassie or silver staining, Western blot, UV absorption, and sandwich ELISA to determine purity, identity, quantity, and bioactivity, respectively. In addition, samples were analyzed by N-terminal amino acid sequencing and amino acid analysis. These analyses provided confirmation of identity and quantity of the purification products.

Representative SDS-PAGE and Western blot profiles of the purified WN-80E protein are presented in FIG. 2. For the analysis, samples were run under non-reducing conditions. The WN-80E molecule migrates as a single band with a relative molecular weight consistent with that determined from the amino acid composition (i.e., 43 kD).

Example 2

Production of WN-80E Under cGMP to Support Clinical Testing

A Master Cell Bank (MCB) was prepared from S2 cells transformed with the pMttprMWN80E plasmid under cGMP conditions. The cGMP manufacturing process involves expansion of the S2 MCB cell line to a stirred tank bioreactor and then harvesting the culture medium containing the secreted protein. The cells are separated from the culture medium by filtration utilizing depth filters. The WN-80E is then purified from the resultant clarified supernatant by immunoaffinity chromatography using the 4G2 monoclonal antibody. The immunoaffinity purification product is subsequently taken through a low pH viral inactivation step and a viral filtration step using PVDF membranes with pore sizes capable of removing 20 nm particles. The final processing of the WN-80E protein involves buffer-exchange and concentration by ultrafiltration followed by a final filtration through a 0.2 µm filter.

The manufacture of a representative lot of WN-80E under cGMP was accomplished as described below. Vials of the MCB were thawed and cultured in a 10 mL volume of EX-CELL medium for 5 days at 26° C. Each culture was expanded to disposable shake flasks. The cultures were grown until a cell density of $1.5 \times 10^7$/mL was achieved. Flasks were pooled and used to inoculate a larger culture in a disposable shake flask which was then grown until a density of $2 \times 10^7$ cells/mL was achieved. The culture was then expanded to multiple cultures in disposable shake flasks. These cultures were grown until an average cell density of $1.6 \times 10^7$ cells/mL was achieved. The cells from the flasks were pooled and used to inoculate a 20 L stainless steel bioreactor. The culture was grown until a cell density of $1.2 \times 10^7$ cells/mL was achieved. The appropriate amount of cells from the 20 L bioreactor were transferred to a 100 L stainless steel bioreactor to achieve an initial cell density of $2 \times 10^6$ cells/mL. The culture was grown until a cell density of $>4.0 \times 10^6$ cells/mL was achieved. The culture was then induced by adding copper sulfate to the culture to achieve a final concentration of 0.2 mM. The culture was then grown for 5 days. The 100 L of culture was harvested by depth filtration using a 0.45 µm filter cartridge which was followed by a 0.2 µm filter cartridge. The filtrate was collected in 10 L volumes in single use bags and stored at −20° C.

The WN-80E bulk harvest was thawed and particulates were removed by passage of the material through a 5 µm pore size filter. The filtered bulk harvest was loaded directly onto a 4G2-sepharose column. After loading, the column was washed with 11 mM PBS, pH 7.1, containing 0.05% Tween-20 (PBST) then retained WN-80E was eluted by lowering the pH with a glycine buffer. Sub-batches were pooled then treated for viral inactivation by lowering the pH to a final pH of 3.8 and incubating the material at ambient temperature (15-25° C.) for 16-24 hours after which the pH was adjusted to 7.0±0.5. The material was passed through a 0.2 µm pre-filter to remove small particulates then filtered using a 20 nm pore sized membrane. The material was then concentrated and buffered exchanged by ultrafiltration and a final sterile filtration was accomplished by passage through a 0.2 µm filter directly into sterile bags. The purified WN-80E biologic substance underwent extensive safety, identity, strength, and purity assessments prior to release for formulation into HBV-002 vaccine.

Example 3

Formulation of the HBV-002 Vaccine for Use in Clinical Studies

The purified WN-80E biologic substance described in Example 2 was thawed and transferred into a Class 100 laminar flow area. The WN-80E was added to a sterile container and sterile Dulbecco's Phosphate Buffered Saline (DPBS) was added in to achieve a final protein target concentration of 0.20 mg/mL. The diluted WN-80E solution was sterile filtered. Alhydrogel '85 was volumetrically added to a sterile container containing DPBS to a final Alhydrogel concentration of 14.0 mg/mL. The WN-80E protein solution was then transferred quantitatively into the Alhydrogel suspension and mixed gently overnight at 2-8° C.

Following the overnight adsorption the quantity of WN-80E protein which was not adsorbed was determined. A minimum of 75% adsorption was required to move forward to fill of the HBV-002 vaccine. The HBV-002 vaccine was dispensed into prepared sterile vials. The filled vials were stoppered, sealed, and crimped. The filled vials of HBV-002 vaccine were stored at 2 to 8° C. Extensive safety, strength, identity, potency, and purity testing was conducted prior to use of the HBV-002 vaccine in clinical studies.

Example 4

Clinical Testing of the HBV-002 West Nile Recombinant Subunit Vaccine

The HBV-002 vaccine manufactured under cGMP as described in Example 3 was tested in a clinical trial. The Phase 1, open-label, clinical study of HBV-002 biologic product in healthy adult volunteers evaluated three different dose levels of the vaccine's active ingredient (WN-80E) with the same amount of Alhydrogel '85 adjuvant or the highest dose level of WN-80E without Alhydrogel '85. Subjects received a single IM injection of study vaccine at Weeks 0, 4 and 8. The design of the study is summarized in Table 1 below.

TABLE 1

| Design of the Clinical Study HBV-002-C-101 | |
| --- | --- |
| Treatment | Cohort |
| Low Dose WN-80E (5 µg) + Alhydrogel (3.5 mg) | Cohort A (N = 6) |
| Medium Dose WN-80E (15 µg) + Alhydrogel (3.5 mg) | Cohort B (N = 6) |
| High Dose WN-80E (50 µg) + Alhydrogel (3.5) | Cohort C (N = 6) |
| High Dose WN-80E (50 µg), no adjuvant | Cohort D (N = 6) |

Safety and tolerability were assessed throughout the study by targeted physical examination, routine laboratory testing (hematology, clinical chemistry and urinalysis) and the recording of vital signs and adverse events in study volunteers. In addition, subjects used diary cards for 14+/−2 days after each vaccination to record reactogenicity and tolerance data as well as specific adverse events. Efficacy assessments in this study included the determination of the rate and extent of virus neutralizing antibody titers (i.e., immunogenicity), as determined by $PRNT_{50}$ (plaque reduction neutralization test) assay of ≥1:10.

The clinical safety assessments showed that the vaccine was well tolerated with no severe adverse events throughout the dosing period. The major side effects noted were mild injection site reactions (e.g. pain, swelling) which were generally of short duration (1-3 days). There were almost no systemic adverse events associated with the vaccine and those few events which were associated with the vaccine (e.g. headache) were mild in nature and of very short duration (several hours). This demonstrates that the HBV-002 vaccine has a very acceptable safety profile and would be appropriate for frail and at-risk populations such as the elderly and immunocompromised.

The efficacy assessments (measurement of virus neutralizing antibody) demonstrated that all subjects (100%) which received the HBV-002 vaccine formulation containing Alhydrogel '85, regardless of dose, developed virus neutralizing antibody titers ≥10 when tested at 2 weeks post dose 3. Many of the subjects that received the vaccine at doses of 15 or 50 μg developed virus neutralizing antibody titers by post dose 2. The virus neutralizing antibody responses induced by the HBV-002 vaccine are illustrated in FIG. 3.

This demonstrates that this particularly safe vaccine is also particularly effective and overcomes the technical problem of inducing relevant protective immune responses in vaccinated individuals while maintaining an acceptable safety profile in particular for those subjects at highest risk of severe disease, the elderly and immunocompromised. Furthermore, this relevant protective immune response was induced in vaccinated individuals without the inclusion of NS1 in the formulation, despite the anticipated requirement for NS1 for potent protection (McDonell et al., U.S. Pat. No. 6,416,763).

REFERENCES

Bancroft, W. H. et al., (1984) *Vaccine* 149:1005-10
Barrett, ADT and Teuwen, DE, (2009) *Curr. Opin. Immunol.* 21:308-313
Beasley, D. et al., (2004) *Vaccine* 22:3722-26
Ben-Nathan et al., (2003) *J. Inf. Dis.* 188:5-12
Bray, M. et al., (1996) *J Virol.* 70:4162-66
Bray, M. and Lai, C. J. (1991) *Proc. Natl. Acad. Sci. USA* 88:10342-46
Chambers, T. J. et al., (1990) *Annual Rev. Microbiol.* 44:649-88
Chen, W. et al., (1995) *J. Virol.* 69:5186-90
Chowers et al., (2001) *Emerg. Inf. Dis.* 7:675-78
Comment (2004) *Ann. Inter. Med.* 141:153
Culp, J. S. et al., (1991) *Biotechnology* 9:173-7
Cuzzubbo et al., (2001) *Clin. Diagn. Lab. Immunol.* 8:1150-55
Diamond, M. S. et al., (2008) *Immunol. Rev.* 225:212-225
Eckels, K. H., and Putnak, R. (2003) *Adv. Virus Res.* 61:395-418
Heinz, F. X. et al., (1983) *Virology* 130:485-501
Henchal, E. A. et al., (1985) *Am. J. Trop. Med. Hyg.* 34:162-69
Henchal, E. A. and Putnak J. R. (1990) *Clin. Microbiol Rev.* 3:376-96
Ivey-Hoyle, M. (1991) *Curr. Opin. Biotechnol.* 2:704-7
Ivy, J. et al., U.S. Pat. No. 6,432,411
Johansen, H. et al., (1989) *Genes Dev.* 3:882-89
Kimura-Kiroda, J. and K. Yasui (1988) *J. Immunol.* 141:3606-10
Klee et al., (2004) *Emerg. Inf. Dis.* 10:1405-11
Kreil et al., (1998) *J. Virol.* 72:3076-3081
Lai, C. J. et al., (1998) *Clin. Diagn. Virol.* 10:173-79
Lai, C. J. and Monath, T. P. (2003) *Adv. Virus Res.* 61:469-509
Lieberman, M. et al. (2008) *Vaccine* 25:414-23
Lieberman, M. et al. (2009) *Clin. Vaccine Immunol.* 16:1332-37
Markoff, L. (2000) *Vaccine* 18:26-32
Martin, J. E. et al., (2007) *J. Infect. Dis.* 196:1732-40
Mason, P. W. (1989) *J. Gen. Virol.* 70:2037-48
McDonell et al., U.S. Pat. No. 6,416,763
McKee, K. T. et al., (1987) *Am. J Trop. Med. Hyg.* 36:435-42
Modis, Y. et al., (2003) *Proc. Natl. Acad Sci. USA* 100:6986-91
Modis, Y. et al., (2004) *Nature* 427:313-9
Monath, T. P., et al., (2006) *Proc. Natl. Acad. Sci. USA* 103:6694
Morbidity and Mortality Weeldy Report (MMWR) (2004) vol. 53, Nov. 19, 2004
Morbidity and Mortality Weekly Report (MMWR) (2008) vol. 57:720-23
Money, J. D. et al., *J. Inf. Dis.* 194:1300-8
Murphy et al., (1986) *J. Clin. Microbiol.* 24:197-202
Platonov et al., (2001) *Emerg. Inf. Dis.* 7:128-32
Pletnev et al., (2002) *Proc. Natl. Acad. Sci. USA* 99:3036-41
Putnak, R., et al., (2003) *Adv. Virus Res.* 61:445-68
Review (2003) *Am. J. Trop. Med. Hyg.* 69 Supplement: 1-60
Sanchez et al., (2006) *FEMS Immunol. Med. Microbiol.* 24:4914-26
Siirin, M. T. et al., (2008) *Am. J. Trop. Med. Hyg.* 79:955-62

We claim:

1. A vaccine comprising:
an effective amount of purified protein as set forth in SEQ ID NO:1 and an effective amount of aluminum hydroxide adjuvant, formulated in dosage form of 15-50 ug per dose, and wherein the vaccine induces the production of neutralizing antibodies for West Nile virus in human subjects.

2. The vaccine of claim 1 wherein the E polypeptide is recombinantly produced and expressed in insect host cells.

3. The vaccine of claim 2 wherein the insect cells are *Drosophila melanogaster* Schneider 2 (S2) cells.

4. The vaccine of claim 1, further comprising a pharmaceutically acceptable excipient.

5. The vaccine of claim 1 for use in subjects who have immunodeficiences as opposed to healthy subjects.

6. The vaccine of claim 1, wherein at least 75% of the protein of SEQ ID NO:1 is adsorbed to the adjuvant.

7. The vaccine of claim 1, wherein the dosage form is selected from 15 ug/dose or 50 ug/dose.

* * * * *

SEQUENCE LISTING

<160> NUMBER OF SEQ ID NOS: 1

<210> SEQ ID NO 1
<211> LENGTH: 401
<212> TYPE: PRT
<213> ORGANISM: West Nile Virus

<400> SEQUENCE: 1

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met

```
                    35                   40                   45
Glu Ala Ala Asn Leu Ala Glu Val Arg Ser Tyr Cys Tyr Leu Ala Thr
                50                   55                   60
Val Ser Asp Leu Ser Thr Lys Ala Ala Cys Pro Thr Met Gly Glu Ala
 65                   70                   75                   80
His Asn Asp Lys Arg Ala Asp Pro Ala Phe Val Cys Arg Gln Gly Val
                    85                   90                   95
Val Asp Arg Gly Trp Gly Asn Gly Cys Gly Leu Phe Gly Lys Gly Ser
                100                  105                  110
Ile Asp Thr Cys Ala Lys Phe Ala Cys Ser Thr Lys Ala Ile Gly Arg
                115                  120                  125
Thr Ile Leu Lys Glu Asn Ile Lys Tyr Glu Val Ala Ile Phe Val His
                130                  135                  140
Gly Pro Thr Thr Val Glu Ser His Gly Asn Tyr Ser Thr Gln Val Gly
145                  150                  155                  160
Ala Thr Gln Ala Gly Arg Phe Ser Ile Thr Pro Ala Ala Pro Ser Tyr
                    165                  170                  175
Thr Leu Lys Leu Gly Glu Tyr Gly Glu Val Thr Val Asp Cys Glu Pro
                    180                  185                  190
Arg Ser Gly Ile Asp Thr Asn Ala Tyr Tyr Val Met Thr Val Gly Thr
                    195                  200                  205
Lys Thr Phe Leu Val His Arg Glu Trp Phe Met Asp Leu Asn Leu Pro
210                  215                  220
Trp Ser Ser Ala Gly Ser Thr Val Trp Arg Asn Arg Glu Thr Leu Met
225                  230                  235                  240
Glu Phe Glu Glu Pro His Ala Thr Lys Gln Ser Val Ile Ala Leu Gly
                    245                  250                  255
Ser Gln Glu Gly Ala Leu His Gln Ala Leu Ala Gly Ala Ile Pro Val
                    260                  265                  270
Glu Phe Ser Ser Asn Thr Val Lys Leu Thr Ser Gly His Leu Lys Cys
                    275                  280                  285
Arg Val Lys Met Glu Lys Leu Gln Leu Lys Gly Thr Thr Tyr Gly Val
                    290                  295                  300
Cys Ser Lys Ala Phe Lys Phe Leu Gly Thr Pro Ala Asp Thr Gly His
305                  310                  315                  320
Gly Thr Val Val Leu Glu Leu Gln Tyr Thr Gly Thr Asp Gly Pro Cys
                    325                  330                  335
Lys Val Pro Ile Ser Ser Val Ala Ser Leu Asn Asp Leu Thr Pro Val
                    340                  345                  350
Gly Arg Leu Val Thr Val Asn Pro Phe Val Ser Val Ala Thr Ala Asn
                    355                  360                  365
Ala Lys Val Leu Ile Glu Leu Glu Pro Pro Phe Gly Asp Ser Tyr Ile
                    370                  375                  380
Val Val Gly Arg Gly Glu Gln Gln Ile Asn His His Trp His Lys Ser
385                  390                  395                  400
Gly
```